US011479833B2

(12) United States Patent
Marie et al.

(10) Patent No.: US 11,479,833 B2
(45) Date of Patent: Oct. 25, 2022

(54) CARBAMIDES FOR SEPARATING URANIUM(VI) AND PLUTONIUM(IV) WITHOUT REDUCING THE PLUTONIUM(IV)

(71) Applicants: COMMISSARIAT À L'ÉNERGIE ATOMIQUE ET AUX ÉNERGIES ALTERNATIVES, Paris (FR); Orano Cycle, Courbevoie (FR); ELECTRICITE DE FRANCE, Paris (FR)

(72) Inventors: Cécile Marie, Avignon (FR); Clémence Berger, Avignon (FR); Guillaume Mossand, Avignon (FR); Emilie Russello, Bagnols sur Ceze (FR); Eugen Andreiadis, Avignon (FR); Dominique Guillaumont, Avignon (FR); Manuel Miguirditchian, Avignon (FR); Christian Sorel, Villeneuve les Avignon (FR)

(73) Assignees: COMMISSARIAT A L'ÉNERGIE ATOMIQUE ET AUX ÉNERGIES, Paris (FR); ORANO CYCLE, Châtillon (FR); ELECTRICITE DE FRANCE, Paris (FR)

( * ) Notice: Subject to any disclaimer, the term of this patent is extended or adjusted under 35 U.S.C. 154(b) by 246 days.

(21) Appl. No.: 16/625,557

(22) PCT Filed: Jun. 28, 2018

(86) PCT No.: PCT/FR2018/051606
§ 371 (c)(1),
(2) Date: Dec. 20, 2019

(87) PCT Pub. No.: WO2019/002788
PCT Pub. Date: Jan. 3, 2019

(65) Prior Publication Data
US 2021/0363609 A1 Nov. 25, 2021

(30) Foreign Application Priority Data
Jun. 29, 2017 (FR) .................................. 17 56057

(51) Int. Cl.
| C22B 60/00 | (2006.01) |
| C22B 60/02 | (2006.01) |
| C22B 3/26 | (2006.01) |
| C22B 60/04 | (2006.01) |
| G21C 19/46 | (2006.01) |

(52) U.S. Cl.
CPC .............. *C22B 60/026* (2013.01); *C22B 3/26* (2021.05); *C22B 60/04* (2013.01); *G21C 19/46* (2013.01)

(58) Field of Classification Search
CPC ... C22B 60/0239; C22B 60/026; C22B 60/04; C22B 3/26
See application file for complete search history.

(56) References Cited

U.S. PATENT DOCUMENTS

| 2,993,930 | A | | 7/1961 | Chappelow et al. |
| 3,285,943 | A | * | 11/1966 | Lindland ................ C01G 43/00 |
| | | | | 534/11 |
| 3,868,354 | A | | 2/1975 | Halasa |
| 2013/0202501 | A1 | | 8/2013 | Saudray et al. |
| 2018/0218798 | A1 | | 8/2018 | Miguirditchian et al. |
| 2018/0222849 | A1 | | 8/2018 | Miguirditchian et al. |

FOREIGN PATENT DOCUMENTS

| EP | 0 583 637 B1 | 3/1997 |
| EP | 2 862 852 B1 | 7/2018 |
| WO | 2017/017193 A1 | 2/2017 |
| WO | 2017/017207 A1 | 2/2017 |

OTHER PUBLICATIONS

E. K. Dukes et T. H. Sidall, "Tetrabutyl urea as an extractant for nitric acid and some actinide nitrates", Journal of Inorganic and Nuclear Chemistry 1966, 28(10), pp. 2307-2312.
G. M. Chumakova et al., "Extraction of uranium and transuranium elements from nitric acid solutions of carbonyl-containing compounds", Radiokhimiya 1980, 22(2), pp. 213-217.
B. G. Vats et al., "Selective recognition of uranyl ions from bulk of thorium(IV) and lanthanise(III) ions by tetraalkyl urea: a combined experimental and quantum chemical study", Dalton Transactions 2016, 45(25), pp. 10319-10325.
XP-002779376 « Urea, N-cyclohexyl-N'-cyclopropyl-N-(cyclopropylmethyl)- », RN 1333879-14-3.
XP-002779377 « Urea, N'-cyclohexyl-N-cyclopropyl-N-(cyclopropylmethyl)- », RN 1714202-13-7.
XP-002779378 « Urea, N'-cyclohexyl-N,N-bis(cyclopropylmethyl)- », RN 1713937-70-2.
XP-002779379 « Urea, N'-cyclopentyl-N,N-bis(cyclopropylmethyl)- », RN 1713937-68-8.
XP-002779380 « Urea, N'-cyclopropyl-N,N-bis(cyclopropylmethyl)- », RN 1594026-30-8.
International Search Report for International Application No. PCT/FR2018/051606, dated Nov. 13, 2018.
(Continued)

Primary Examiner — Steven J Bos
(74) Attorney, Agent, or Firm — Pearne & Gordon LLP

(57) ABSTRACT

The use of carbamides as extractants for fully or partially separating uranium(VI) from plutonium(IV) in an aqueous solution obtained by dissolving a spent nuclear fuel in nitric acid, by method of liquid-liquid extraction, without carrying out any reduction of the plutonium(IV) to plutonium(III). The invention also relates to new carbamides. Uses are the processing of spent nuclear fuels based on uranium (especially uranium oxides—UOX) or uranium and plutonium (especially mixed uranium and plutonium oxides—MOX).

13 Claims, 1 Drawing Sheet

(56) References Cited

OTHER PUBLICATIONS

Written Opinion for International Application No. PCT/FR2018/051606, dated Nov. 13, 2018.
Preliminary French Search Report for Application No. 17 56057, dated Mar. 21, 2018.
U.S. Appl. No. 16/479,830; entitled "Dissymmetric N,N-Dialkylamides Used Particularly For Separating Uranium(VI) From Plutonium(IV), Synthesis Thereof And Uses Of Same"; filed Jul. 22, 2019.

* cited by examiner

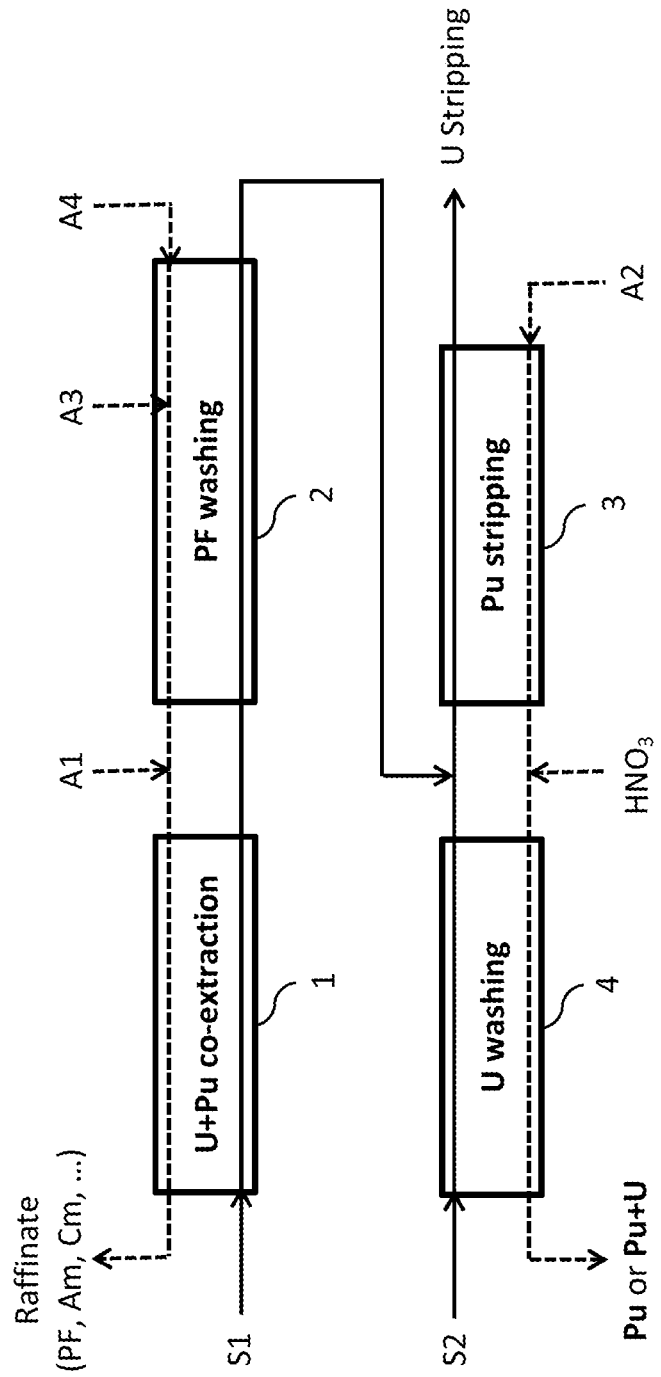

CARBAMIDES FOR SEPARATING URANIUM(VI) AND PLUTONIUM(IV) WITHOUT REDUCING THE PLUTONIUM(IV)

CROSS-REFERENCE TO RELATED APPLICATIONS

This is a National Stage application of PCT international application PCT/FR2018/051606, filed on Jun. 28, 2018, which claims the priority of French Patent Application No. 17 56057, filed Jun. 29, 2017, both of which are incorporated herein by reference in their entireties.

FIELD OF THE INVENTION

The invention relates to the field of spent nuclear fuel treatment.

More specifically, the invention relates to the use of carbamides (i.e. urea derivatives) as extractants for totally or partially separating uranium(VI) from plutonium(IV) using an aqueous solution issued from the dissolution of a spent nuclear fuel in nitric acid, by liquid-liquid extraction, without performing any reduction of plutonium(IV) to plutonium (III).

It also relates to novel carbamides endowed with extremely advantageous extractant properties.

The invention particularly finds an application in the treatment of spent nuclear fuels based on uranium (particularly uranium oxides—UOX) or uranium and plutonium (particularly mixed uranium and plutonium oxides—MOX).

STATE OF THE RELATED ART

The PUREX method, which is used in all the spent nuclear fuel treatment plants in existence worldwide (La Hague in France, Rokkasho in Japan, Sellafield in the United Kingdom, etc.), uses tri-n-butyl phosphate (or TBP) as an extractant, to recover uranium(VI) and plutonium(IV), by liquid-liquid extraction, from aqueous solutions issued from the dissolution of these fuels in nitric acid.

In this method, TBP is used in 30% (v/v) solution in an aliphatic diluent (hydrogenated tetrapropylene (or TPH), n-dodecane or kerosene). This organic solution is commonly referred to as a "solvent" in the field in question.

The recovery of uranium and plutonium using the PUREX method is performed in a plurality of cycles:
- a first uranium(VI) and plutonium(IV) purification cycle (known as "1CUPu"), which is intended to decontaminate these elements from americium, curium and fission products with partitioning of uranium(VI) and plutonium(IV) into two aqueous streams as of this first cycle;
- a second uranium(VI) purification (known as "2CU"), which is intended to complete the decontamination of this element to meet the specifications defined by the ASTM standards for uranium, the finished product; and
- a second cycle and, in the case of certain plants, a third plutonium(IV) purification cycle (known as "2CPu" and "3CPu", respectively), which are intended to complete the decontamination of this element to meet the specifications defined by the ASTM standards for plutonium, the finished product, and to concentrate same prior to the conversion thereof into oxide $PuO_2$.

The performances of the PUREX method are satisfactory and the feedback acquired since the commissioning of the plants using same is positive.

The use of TBP has limitations, however, which counter the possibility of meeting with this extractant the targets in respect of simplicity, compact design and enhanced safety set for future spent nuclear fuel treatment plants.

The main limitation stems from the fact that partitioning uranium and plutonium into two aqueous streams necessitates reducing plutonium(IV) to plutonium(III) (as, with TBP, the separation factor between uranium(VI) and plutonium(IV) is insufficient, regardless of the acidity of the aqueous solution which is used to carry out this partitioning) and, hence, using large quantities of reducing and anti-nitrous agents, which generate by degradation unstable and reactive species and are therefore restrictive in terms of safety.

The provision of extractants suitable for co-extracting quantitatively uranium and plutonium from an aqueous solution issued from the dissolution of a spent nuclear fuel in nitric acid and then carrying out total or partial separation of these two elements without having to reduce plutonium (IV) to plutonium(III) has therefore given rise to a number of works.

Thus have been proposed the use of symmetrical N,N-dialkylamides, such as N,N-di(2-ethylhexyl)-3,3-dimethylbutanamide (or DEHDMBA), in international PCT application WO 2017/017207, hereinafter reference [1], and that of "dissymmetrical" N,N-dialkylamides, such as N-methyl-N-octyl-2-ethylhexanamide (or MOEHA), in international PCT application WO 2017/017193, hereinafter reference [2]. In both cases, the N,N-dialkylamides exhibit very advantageous performances.

Moreover, three studies relating to the extraction of uranium(VI) and plutonium(IV) of an aqueous nitric solution by carbamides have been published in the literature. These consist of the study conducted by E. K. Dukes and T. H. Sidall with N,N,N',N'-tetra-n-butylurea, which is reported in *Journal of Inorganic and Nuclear Chemistry* 1966, 28(10), 2307-2312, hereinafter reference [3], the study conducted by G. M. Chumakova et al., also with N,N,N',N'-tetra-n-butylurea, which is reported in *Radiokhimiya* 1980, 22(2), 213-217, hereinafter reference [4], and the more recent study conducted by B. G. Vats et al. with N,N-diethyl-N',N'-diisobutylurea (or DEDiBU) and N,N-diethyl-N',N'-di-n-octylurea (or DEDOU), which is reported in *Dalton Transactions* 2016, 45(25), 10319-10325, hereinafter reference [5].

These studies have demonstrated the potential of tetraalkylated carbamides as extractants of uranium(VI) and plutonium(IV). However, none of these indicates the possibility of using this type of compounds to co-extract uranium(VI) and plutonium(IV) from an aqueous solution issued from the dissolution of a spent nuclear fuel, then to totally or partially separate uranium(VI) from plutonium(IV), without having to reduce plutonium(IV) to plutonium(III).

However, within the scope of their research, the Inventors actually observed that some carbamides have extractant properties such that:
- in the presence of an aqueous phase of strong acidity such as that exhibited by aqueous solutions issued from the dissolution of spent nuclear fuels in nitric acid, they result in distribution coefficients of uranium(VI) and plutonium(IV) suitable for enabling quantitative co-extraction of these two elements of this aqueous phase, and
- in the presence of an aqueous phase of moderate acidity, they result in U(VI)/Pu(IV) separation factors suitable for enabling separation of uranium(VI) from plutonium (IV) without it being necessary to reduce plutonium (IV) to plutonium(III), this separation optionally being total or partial as desired.

The present invention is based on these observations.

DESCRIPTION OF THE INVENTION

The invention firstly relates to the use of a carbamide of general formula (I):

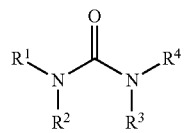

wherein:

$R^1$, $R^2$ and $R^3$, identical or different, represent a linear or branched alkyl group, comprising from 1 to 12 carbon atoms, a cycloalkyl group comprising from 3 to 12 carbon atoms or a cycloalkylalkyl group comprising from 4 to 13 carbon atoms;

$R^4$ represents a hydrogen atom, a linear or branched alkyl group, comprising from 1 to 12 carbon atoms, a cycloalkyl group comprising from 3 to 12 carbon atoms or a cycloalkylalkyl group comprising from 4 to 13 carbon atoms;

as an extractant for totally or partially separating uranium (VI) from plutonium(IV), without reducing plutonium(IV) to plutonium(III), from an aqueous solution A1 issued from the dissolution of a spent nuclear fuel in nitric acid.

This use comprises:

a) a co-extraction of uranium(VI) and plutonium(IV) from the aqueous solution, the co-extraction comprising at least one contacting, in an extractor, of the aqueous solution A1 with an organic solution S1 comprising the carbamide in an organic diluent, followed by separating the aqueous and organic solutions;

b) a stripping of plutonium(IV) and a fraction of uranium (VI) from the organic solution issued from a), the stripping comprising at least one contacting, in an extractor, of the organic solution 51 with an aqueous solution A2 comprising from 0.1 mol/L to 0.5 mol/L of nitric acid, followed by separating the organic and aqueous solutions; and c) an extraction of all or part of the uranium(VI) fraction present in the aqueous solution issued from b), the extraction comprising at least one contacting, in an extractor, of the aqueous solution with an organic solution S2 comprising the carbamide in an organic diluent, followed by separating the aqueous and organic solutions; whereby an aqueous solution comprising plutonium(IV) without uranium(VI) or a mixture of plutonium(IV) and uranium(VI), and an organic solution comprising uranium(VI) without plutonium(IV) are obtained.

Hereinabove and hereinafter, the expressions "comprising from . . . to . . . ", "ranging from . . . to . . . " and "between . . . and . . . " are equivalent and denote that the bounds are included.

There is understood by "linear or branched alkyl group, comprising from 1 to 12 carbon atoms", any linear or branched chain alkyl group that comprises 1, 2, 3, 4, 5, 6, 7, 8, 9, 10, 11 or 12 carbon atoms such as a methyl, ethyl, n-propyl, isopropyl, n-butyl, sec-butyl, isobutyl, Cert-butyl, n-pentyl, sec-pentyl, isopentyl, n-hexyl, isohexyl, n-heptyl, isoheptyl, n-octyl, isooctyl, n-nonyl, isononyl, n-decyl, isodecyl, n-undecyl, n-dodecyl, 2-methylbutyl, 2-methylpentyl, 3-methyl-pentyl, 2-methylhexyl, 3-methylhexyl, 2-methylheptyl, 2-methyloctyl, 2-ethylhexyl, 1,5-dimethylhexyl, 2,4,4-trimethylpentyl, 2-ethylheptyl, 1,2-dimethylheptyl, 2,6-dimethylheptyl, 3,5,5-trimethylhexyl, 2-methylnonyl, 3,7-dimethyloctyl, 2,4,6-trimethylheptyl, 2-butylhexyl group, etc.

There is understood by "cycloalkyl group comprising from 3 to 12 carbon atoms", any cycloalkyl group with one or a plurality of fused or bridged rings, this or these rings optionally being substituted by one or a plurality of alkyl groups, insofar as the total number of carbon atoms comprised by this cycloalkyl group (with the substituents if it has substituents) is equal to 3, 4, 5, 6, 7, 8, 9, 10, 11 or 12; such a cycloalkyl group is, for example, a cyclopropyl, cyclobutyl, cyclopentyl, cyclohexyl, cycloheptyl, cyclooctyl, decahydronaphthalenyl, bicyclopropyl, bicyclohexyl group, a cyclopentyl or cyclohexyl group substituted by one or a plurality of methyl, ethyl, n-propyl, iso-propyl, n-butyl, iso-butyl, Cert-butyl, sec-butyl groups, etc.

There is understood by "cycloalkylalkyl group comprising from 4 to 13 carbon atoms", any linear or branched chain alkyl group which is substituted by a cycloalkyl group, insofar as the total number of carbon atoms comprised by this alkyl group with the substituent thereof is equal to 4, 5, 6, 7, 8, 9, 10, 11, 12 or 13; such a cycloalkylalkyl group is, for example, a 3-cyclohexylpropyl, 3-cyclohexyl-butyl, 3-cyclohexyl-2-methylbutyl, 4-cyclohexyl-1-methylbutyl, 4-cyclohexyl-2-methylbutyl, 4-cyclohexyl-3-methylbutyl, 4-cyclohexyl-1-ethylbutyl, 4-cyclohexyl-2-ethylbutyl, 4-cyclohexyl-1-propylbutyl, 4-cyclohexyl-2-propylbutyl, 4-cyclohexyl-pentyl, 4-cyclohexyl-2-methylpentyl group, etc.

Moreover, the expressions "aqueous solution" and "aqueous phase" are equivalent and interchangeable, as the expressions "organic solution" and "organic phase" are equivalent and interchangeable.

Insofar as the cycloalkyl groups can be considered as alkyl groups wherein the sole carbon chain or the main carbon chain is cyclic, the carbamide suitable for use according to the invention may be described as tetraalkylated carbamide when $R^4$ is different to a hydrogen atom, or indeed trialkylated carbamide when $R^4$ represents a hydrogen atom. This description will therefore be used hereinafter.

According to the invention, the total number of carbon atoms comprised in the carbamide is preferentially between 17 and 25.

When the carbamide is tetraalkylated, then it is preferred that $R^1$, $R^2$, $R^3$ and $R^4$ represent a linear or branched alkyl group, comprising from 1 to 12 carbon atoms.

Moreover, it is preferred:

that $R^1$ and $R^2$ are identical and that $R^3$ and $R^4$ are identical while being different to $R^1$ and $R^2$, or indeed that $R^1$ and $R^4$ are identical and that $R^2$ and $R^3$ are identical while being different to $R^1$ et $R^4$, or indeed that $R^1$, $R^2$, $R^3$ and $R^4$ are all identical.

When $R^1$ and $R^2$ are identical and $R^3$ and $R^4$ are identical while being different to $R^1$ and $R^2$, then $R^1$ and $R^2$ represent preferentially a linear or branched alkyl group, comprising from 1 to 5 carbon atoms, whereas $R^3$ and $R^4$ represent preferentially a linear or branched alkyl group, comprising from 6 to 10 carbon atoms, the total number of carbon atoms comprised by the carbamide being then, preferably, equal to 19, 21 or 23.

Similarly, when $R^1$ and $R^4$ are identical and $R^2$ and $R^3$ are identical while being different to $R^1$ and $R^4$, then $R^1$ and $R^4$ represent preferentially a linear or branched alkyl group, comprising from 1 to 5 carbon atoms, whereas $R^2$ and $R^3$ represent preferentially a linear or branched alkyl group, comprising from 6 to 10 carbon atoms, the total number of carbon atoms comprised by the carbamide being, here also, preferably equal to 19, 21 or 23.

When $R^1$, $R^2$, $R^3$ and $R^4$ are identical, then $R^1$, $R^2$, $R^3$ and $R^4$ represent preferentially a linear or branched alkyl group comprising from 4 to 8 carbon atoms, the n-butyl, n-pentyl, n-hexyl, n-heptyl and n-octyl groups being particularly preferred.

When the carbamide is trialkylated, then it is preferred that $R^1$, $R^2$ and $R^3$ represent a linear or branched alkyl group, comprising from 1 to 12 carbon atoms, preferably from 2 to 10 carbon atoms and, even more preferably, from 4 to 8 carbon atoms.

Moreover, it is preferred that $R^1$ is identical to $R^2$ and, more preferably, that $R^1$, $R^2$ and $R^3$ are all identical, in which case $R^1$, $R^2$ and $R^3$ represent, preferably, a linear or branched alkyl group, comprising from 6 to 8 carbon atoms, the n-hexyl, n-heptyl, n-octyl and 2-ethylhexyl groups being particularly preferred.

Thus, by way of examples of preferred carbamides, mention may be made of:

N,N,N',N'-tetra-n-butylurea (or TBU), which complies with the general formula (I) wherein $R^1$, $R^2$, $R^3$ and $R^4$ represent an n-butyl group;

N,N,N',N'-tetra-n-pentylurea (or TPU), which complies with the general formula (I) wherein $R^1$, $R^2$, $R^3$ and $R^4$ represent an n-pentyl group;

N,N,N',N'-tetra-n-hexylurea (or THU), which complies with the general formula (I) wherein $R^1$, $R^2$, $R^3$ and $R^4$ represent an n-hexyl group;

N,N,N',N'-tetra-n-octylurea (or TOU), which complies with the general formula (I) wherein $R^1$, $R^2$, $R^3$ and $R^4$ represent an n-octyl group;

N,N'-di-n-butyl-N,N'-di-n-hexylurea (or DBDHU), which complies with the general formula (I) wherein $R^1$ and $R^4$ represent an n-butyl group and $R^2$ and $R^3$ represent an n-hexyl group;

N,N'-di-n-heptyl-N,N'-di-n-propylurea (or DHDPU), which complies with the general formula (I) wherein $R^1$ and $R^4$ represent an n-propyl group and $R^2$ and $R^3$ represent an n-heptyl group;

N,N'-diethyl-N,N'-di-n-octylurea (or sym-DEDOU), which complies with the general formula (I) wherein $R^1$ and $R^4$ represent an ethyl group and $R^2$ and $R^3$ represent an n-octyl group;

N,N'-dimethyl-N,N'-di-n-nonylurea (or DMDNU), which complies with the general formula (I) wherein $R^1$ and $R^4$ represent a methyl group and $R^2$ and $R^3$ represent an n-nonyl group;

N,N,N'-tri-n-octylurea (or TrOU), which complies with the general formula (I) wherein $R^1$, $R^2$ and $R^3$ represent an n-octyl group and $R^4$ represents a hydrogen atom;

N,N,N'-tri(2-ethylhexyl)urea (or TrEHU), which complies with the general formula (I) wherein $R^1$, $R^2$ and $R^3$ represent a 2-ethylhexyl group and $R^4$ represents a hydrogen atom; and N,N-di(2-ethylhexyl)-N'-n-octylurea (or DEHOU), which complies with the general formula (I) wherein $R^1$ and $R^2$ represent a 2-ethylhexyl group, $R^3$ represents an n-octyl group and $R^4$ represents a hydrogen atom.

Among these carbamides, most preference is given to the carbamides TBU, THU, TPU, DBDHU, DHDPU, sym-DEDOU and DMDNU in that they exhibit a particularly high selectivity for uranium(VI) with respect to plutonium (IV) at moderate acidity, i.e. in the presence of an aqueous phase comprising from 0.1 mol/L to 0.5 mol/L of nitric acid.

According to the invention, the organic solutions S1 and S2 comprise, preferably, from 0.5 mol/L to 2 mol/L and, more preferably, from 1 mol/L to 1.4 mol/L of the carbamide.

The organic diluent is advantageously an acyclic hydrocarbon or a mixture of acyclic hydrocarbons, for example n-dodecane, hydrogenated tetrapropylene (or TPH), kerosene, Isane™ IP-185T or Isane™ IP-175T, preference being given to TPH.

As regards the aqueous solution issued from the dissolution of a spent nuclear fuel in nitric acid, it typically comprises from 3 mol/L to 6 mol/L of nitric acid.

Preferably, step a) further comprises a decontamination of the organic solution issued from the co-extraction of uranium(VI) and plutonium(IV) with respect of americium, curium and fission products, this decontamination comprising at least contacting, in an extractor, of the organic solution with an aqueous solution A3 comprising from 1 mol/L to 6 mol/L of nitric acid, followed by separating the organic and aqueous solutions. This decontamination is optionally supplemented by a deacidification of the decontaminated organic solution, this deacidification comprising at least contacting, in an extractor, of the organic solution issued from the decontamination with an aqueous solution A4 comprising from 0.1 mol/L to 1 mol/L and, more preferably, 0.5 mol/L of nitric acid, followed by separation of the organic and aqueous solutions.

Also preferably, the contacting, in the extractor wherein step b) takes place, of the organic solution issued from step a) with the aqueous solution A2 comprises a counterflow circulation of the organic and aqueous solutions with a flow rate ratio O/A (organic/aqueous) which is advantageously greater than 1, preferably, equal to or greater than 3 and, more preferably, equal to or greater than 5, so as to obtain a concentrating stripping of the plutonium(IV), i.e. a stripping of plutonium(IV) resulting in an aqueous solution wherein the concentration of plutonium(IV) is greater than that exhibited by this element in the organic solution from which it is stripped.

According to the invention, the uranium(VI) which is present in the organic solution issued from step c) may subsequently be stripped from this solution by at least one contacting, in an extractor, of the organic solution with an aqueous solution A5 comprising at most 0.05 mol/L and, more preferably, at most 0.01 mol/L of nitric acid, followed by separating the organic and aqueous solutions. This stripping may be carried out at ambient temperature or at a temperature of 40° C. to 50° C., suitable for promoting the stripping of uranium(VI). It may, moreover, be carried out using a flow rate ratio O/A greater than 1 so that uranium (VI) is stripped in a concentrating fashion.

Of the carbamides suitable for use according to the invention, some such as the tetraalkylated carbamides TBU, THU, TOU and TPU belong to the prior art.

On the other hand, others such as, on one hand, the tetraalkylated carbamides DBDHU, DHDPU, sym-DEDOU and DMDNU, and, on the other, the trialkylated carbamides TrOU, TrEHU and DEHOU have never, to the Inventors' knowledge, been described in the prior art.

Therefore, the subject matter of the invention is that of a tetraalkylated carbamide of general formula (I) hereinabove wherein $R^1$ and $R^4$ are identical and represent a linear alkyl group comprising from 1 to 4 carbon atoms, $R^2$ and $R^3$ are identical and represent a linear alkyl group comprising from 6 to 9 carbon atoms, and the total number of carbon atoms comprised by the carbamide is equal to 21.

This tetraalkylated carbamide may be the carbamide DBDHU, the carbamide DHDPU, the carbamide sym-DEDOU or the carbamide DMDNU, preference being given to the carbamides sym-DEDOU and DMDNU.

In a manner known per se, this tetraalkylated carbamide may particularly be obtained by reacting an N,N'-dialkylurea of formula RNHC(O)NHR wherein R has the same meaning as that of $R^2$ and $R^3$ in the carbamide with a halogenoalkane HalR', for example an iodoalkane IR', where R' has the same meaning as that of $R^1$ and $R^4$ in the carbamide, in an organic medium, for example in tetrahydrofuran and in the presence of a metallic hydride such as sodium hydride.

The invention further relates to a trialkylated carbamide of the particular formula (II):

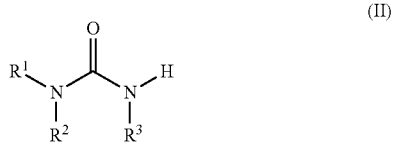

(II)

wherein $R^1$, $R^2$ and $R^3$, identical or different, represent a linear or branched alkyl group, comprising from 8 to 12 carbon atoms or a cycloalkyl group comprising from 3 to 12 carbon atoms, provided that at least one of $R^1$, $R^2$ and $R^3$ is different to a cycloalkyl group.

Here also, the total number of carbon atoms comprised by the carbamide of particular formula (II) is preferentially between 17 and 25.

In this carbamide, it is preferred that $R^1$, $R^2$ and $R^3$ each represent a linear or branched alkyl group, the n-octyl and 2-ethylhexyl groups being most particularly preferred.

Moreover, it is preferred that $R^1$ is identical to $R^2$ and, more preferably, that $R^1$, $R^2$ and $R^3$ are identical to one another.

According to the invention, the carbamide of particular formula (II) is advantageously the carbamide TrOU, the carbamide TrEHU or the carbamide DEHOU, the carbamides TrOU and TrEHU being most particularly preferred.

In a manner known per se, this carbamide may particularly be obtained by reacting a secondary amine of formula $R^1R^2NH$ wherein $R^1$ and $R^2$ are as defined above, with an isocyanate of formula $R^3NCO$ wherein $R^3$ is as defined above, in an organic medium, for example in anhydrous dichloromethane.

Besides having very advantageous extractant properties, the carbamides also have the advantage of only comprising, just like the degradation products thereof, carbon, hydrogen, oxygen and nitrogen atoms such that they are completely incinerable and do not produce penalising secondary waste.

Further features and advantages of the invention will emerge from the following supplementary description.

However, it is obvious that this supplementary description is merely provided by way of illustration and under no circumstance should it be interpreted as a restriction of this subject matter.

BRIEF DESCRIPTION OF THE FIGURE

The drawing FIGURE represents a principle diagram of a preferred embodiment of the use of the invention; in this FIGURE, the rectangles 1 to 4 represent multi-stage extractors such as those conventionally used in the treatment of spent nuclear fuels (mixers-settlers, pulsed columns or centrifugal extractors); the organic phases are symbolised by solid lines whereas the aqueous phases are symbolised by dotted lines.

DETAILED DESCRIPTION OF PARTICULAR EMBODIMENTS

Example I: Synthesis of Tetraalkylated and Trialkylated Carbamides

I.1—N,N'-di-n-butyl-N,N'-di-n-hexylurea or DBDHU:
The carbamide DBDHU is synthesised by:
reacting n-hexylisocyanate (5 mL, 34.3 mmol) with n-hexylamine (0.3 mol/L, 1.2 eq.) in anhydrous dichloromethane to obtain N,N'-di-n-hexylurea; then
reacting N,N'-di-n-hexylurea (7.6 g, 33.4 mmol) with iodobutane (5 eq.) in tetrahydrofuran (THF).

To do this, a solution of n-hexylisocyanate is added dropwise at 0° C. to a solution of n-hexylamine in anhydrous dichloromethane. The reaction mixture is stirred for 1 hour at 0° C. then it is returned to ambient temperature stirred overnight. The solvent is evaporated at reduced pressure and the product is purified on silica gel with a dichloromethane/methanol mixture (95/5, v:v) to give 7.6 g of N,N'-di-n-hexylurea (Yield: >97%).

Then, a suspension of NaH at 60% w/w (8 eq.) in THF is added by portions to a solution of N,N'-di-n-hexylurea in THF at 0° C. The reaction mixture is stirred for 2 hours at 0° C., then iodobutane is added dropwise. The mixture is returned to ambient temperature then refluxed. After one night, the mixture is cooled to 0° C. and supplemented with water. The aqueous phase is extracted with diethyl ether. The organic phase is then washed with a saturated sodium chloride (NaCl) solution then dried on sodium sulphate ($Na_2SO_4$). The solvent is evaporated at reduced pressure and the solid obtained is purified on silica gel with a cyclohexane/ethyl acetate mixture (99/1 to 90/10, v:v) to give 10.5 g of the carbamide DBDHU (Yield: >95%). The characterisations of this carbamide are given hereinafter.

$^1$H NMR ($CDCl_3$, 400 MHz) δ (ppm): 3.12 (m, 8H); 1.50 (m, 8H); 1.28 (m, 16H); 0.92 (m, 12H)
$^{13}$C NMR ($CDCl_3$, 101 MHz) δ (ppm): 165; 48.5; 48.1; 31.6; 30.1; 27.9; 26.7; 22.6; 20.2; 14.0; 13.9
MS (positive mode ESI): 341 ($MH^+$); 682 ($2MH^+$); 703 ($2MNa^+$)
GC-HRMS (positive mode EI): Purity >99%; exact mass calculated for $C_{21}H_{44}N_2O$: 340.3448; obtained: 340.3412

I.2—N,N'-di-n-heptyl-N,N'-di-n-propylurea or DHDPU:
The carbamide DHDPU is synthesised by:
reacting n-heptylisocyanate (5 g, 35.4 mmol) with n-heptylamine (0.3 mol/L, 1.2 eq.) in anhydrous dichloromethane to obtain N,N'-di-n-heptylurea; then
reacting N,N'-di-n-heptylurea (8.8 g, 34.3 mmol) with iodopropane (5 eq.) in THF;
following the same protocol as that described in section 1.1 hereinabove for the synthesis of DBDHU.

This gives 11.2 g of the carbamide DHDPU (Yield: >96%) the characterisations whereof are given hereinafter.
$^1$H NMR ($CDCl_3$. 400 MHz) δ (ppm): 3.07 (m, 8H); 1.50 (m, 8H); 1.25 (m, 16H); 0.86 (m, 12H)
$^{13}$C NMR ($CDCl_3$. 101 MHz) δ (ppm): 163.7; 48.5; 46.7; 30.2; 27.5; 26.4; 25.4; 21.0; 19.6; 12.4; 9.8
MS (positive mode ESI): 341 ($MH^+$); 363 ($MNa^+$); 682 ($2MH^+$); 703 ($2MNa^+$)
GC-HRMS (positive mode EI): Purity 99.1%; exact mass calculated for $C_{21}H_{44}N_2O$: 340.3448; obtained: 340.3438

I.3—NAP-diethyl-N,N'-di-n-octylurea or sym-DEDOU:

The carbamide sym-DEDOU is synthesised by:

reacting n-octylisocyanate (5 g, 32.2 mmol) with n-octylamine (0.3 mol/L, 1.2 eq.) in anhydrous dichloromethane to obtain N,N'-di-n-octylurea; then reacting N,N'-di-n-octylurea (8.9 g, 31.3 mmol) with iodoethane (5 eq.) in THF;

following the same protocol as that described in section 1.1 hereinabove for the synthesis of DBDHU.

This gives 10.2 g of the carbamide sym-DEDOU (Yield: >96%) the characterisations whereof are given hereinafter.

$^1$H NMR (CDCl$_3$, 400 MHz) δ (ppm): 3.14 (q, J=7 Hz, 4H$_{Et}$); 3.07 (m, 4H$_{Oct}$); 1.48 (m, 4H$_{Oct}$); 1.25 (m, 20H$_{Oct}$); 1.08 (t, J=7 Hz, 6H$_{Et}$); 0.86 (m, 6H$_{Oct}$)

$^{13}$C NMR (CDCl$_3$, 101 MHz) δ (ppm): 164.9; 47.8; 42.9; 31.8; 29.4; 29.3; 28.0; 27.1; 22.6; 14.1; 13.2

MS (positive mode ESI): 341 (MH$^+$); 363 (MNa$^+$); 703 (2MNa$^+$)

GC-HRMS (positive mode EI): Purity 99.5%; exact mass calculated for C$_{21}$H$_{44}$N$_2$O: 340.3448; obtained: 340.3437

I.4—N,N'-dimethyl-N,N'-di-n-nonylurea or DMDNU:

The carbamide DMDNU is synthesised by reacting the reaction of N,N'-di-n-methylurea (2 g, 22.7 mmol) with iodononane (5.3 mL, 40.2 mmol, 2 eq.) in THF.

To do this, a solution of N,N'-dimethylurea in THF is added dropwise at 0° C. to a suspension of NaH at 60% w/w (7.2 g, 45.4 mmol, 2 eq.) in THF. The reaction mixture is stirred for 1 hour at 0° C., then iodononane is added dropwise. The mixture is returned to ambient temperature then refluxed. After one night, the medium is cooled to 0° C. and supplemented with water. The aqueous phase is extracted with diethyl ether. The organic phase is then washed with a saturated NaCl solution then dried on Na$_2$SO$_4$. The solvent is evaporated at reduced pressure and the solid obtained is purified on silica gel with a cyclohexane/ethyl acetate mixture (99/1 to 90/10, v:v) to give 7.8 g of the carbamide DMDNU (Yield: >98%). The characterisations of this carbamide are given hereinafter.

$^1$H NMR (CDCl$_3$, 400 MHz) δ (ppm): 3.08 (t, J=7.5 Hz, 4H); 2.76 (s, 6H); 1.52 (m, 4H); 1.25 (m, 24H); 0.87 (m, 6H)

$^{13}$C NMR (CDCl$_3$, 101 MHz) δ (ppm): 165.4; 50.6; 36.5; 31.8; 29.5; 29.4; 29.3; 27.6; 26.9; 22.6; 14.1

MS (positive mode ESI): 341 (MH$^+$); 682 (2MH$^+$); 703 (2MNa$^+$)

GC-HRMS (positive mode EI): Purity 99.2%; exact mass calculated for C$_{21}$H$_{44}$N$_2$O: 340.3448; obtained: 340.3454

I.5—N,N,N'-tri-n-octylurea or TrOU:

The carbamide TrOU is synthesised by reacting di-n-octylamine (1.5 mL, 4.9 mmol, 1 eq.) with n-octylisocyanate (1.7 mL, 9.7 mmol, 2 eq.) in anhydrous dichloromethane (0.1 mol/L).

For this purpose, a solution comprising di-n-octylamine and n-octylisocyanate in anhydrous dichloromethane is stirred for 4.5 hours at ambient temperature. Then, the reaction mixture is washed twice with a 1 M hydrochloric acid (HCl) solution and twice with a saturated sodium bicarbonate (NaHCO$_3$) solution. The organic phase is dried on magnesium sulphate (MgSO$_4$), concentrated at reduced pressure and the residue is purified with flash chromatography on a silica gel with a dichloromethane/ethyl acetate mixture (95/5, v:v) to give 1.9 g of TrOU in the form of a colourless oil (Yield: 100%). The characterisations of this carbamide are given hereinafter.

$^1$H NMR (CDCl$_3$, 400 MHz) δ (ppm): 4.25 (s, 1H); 3.20 (q, J=5.4 Hz, 2H); 3.14 (q, J=7.7 Hz, 4H); 1.50 (m, 6H); 1.46 (m, 30H); 0.87 (t, J=7.2 Hz, 9H)

$^{13}$C NMR (CDCl$_3$, 101 MHz) δ (ppm): 157.8; 47.5; 41.0; 32.0; 30.6; 29.6; 29.5; 29.4; 28.8; 27.2; 22.8; 14.2

IR (KBr, v$_{max}$/cm$^{-1}$): 3345; 2955; 2922; 2853; 1622; 1533; 1465; 1376; 1274; 767; 722

MS (positive mode ESI): 397 (MH$^+$), 816 (2MNa$^+$)

HRMS (positive mode ESI): calculated for C$_{25}$H$_{53}$N$_2$O: 397.4158; obtained: 397.4156

Elemental analysis (%) (C$_{25}$H$_{52}$N$_2$O+0.18AcOEt): calculated: C, 74.88; H, 13.06; N, 6.79; obtained: C, 75.17; H, 12.74; N, 6.88

I.6—N,N,N'-tri(2-ethylhexyl)urea or TrEHU:

TrEHU is synthesised from di(2-ethylhexyl)amine (1.49 mL, 4.92 mmol, 1 eq.) and 2-ethylhexylisocyanate (1.76 mL, 9.84 mmol, 2 eq.) in anhydrous dichloromethane (0.1 mol/L).

For this purpose, a solution comprising di(2-ethylhexyl)amine and 2-ethylhexylisocyanate in anhydrous dichloromethane is stirred for 5 hours at ambient temperature. Then, the reaction mixture is washed twice with a 1 M HCl solution and twice with a saturated NaHCO$_3$ solution. The organic phase is dried on MgSO$_4$, concentrated at reduced pressure and the residue is purified by flash chromatography on silica gel with a dichloromethane/ethyl acetate (99/1 to 90/10, v:v) gradient to give 1.94 g of TrEHU in the form of a thick colourless oil (Yield: 99%). The characterisations of this carbamide are given hereinafter.

$^1$H NMR (CDCl$_3$, 400 MHz) δ (ppm): 4.26 (s, 1H); 3.17 (t, J=5.7 Hz, 2H); 3.09 (m, 4H); 1.62 (m, 2H); 1.46 (m, 25H); 0.88 (m, 18H)

$^{13}$C NMR (CDCl$_3$, 101 MHz) δ (ppm): 158.2; 51.6; 43.6; 39.8; 38.4; 31.2; 30.7; 28.9; 24.4; 24.0; 23.1; 14.1; 11.0; 10.8

IR (KBr, v$_{max}$/cm$^{-1}$): 3348; 2957; 2925; 2859; 1617; 1534; 1459; 1378; 1240; 765; 727

MS (positive mode ESI): 397 (MH$^+$); 816 (2MNa$^+$)

HRMS (positive mode ESI): calculated for C$_{25}$H$_{53}$N$_2$O: 397.4158; obtained: 397.4156

Elemental analysis (%) (C$_{25}$H$_{52}$N$_2$O): calculated: C, 75.69; H, 13.21; N, 7.06; obtained: C, 75.49; H, 13.45; N, 6.91

I.7—N,N-di(2-ethylhexyl)-N'-n-octylurea or DEHOU:

The carbamide DEHOU is synthesised from di(2-ethylhexyl)amine (1.49 mL, 4.92 mmol, 1 eq.) and n-octylisocyanate (1.75 mL, 9.84 mmol, 2 eq.) in anhydrous dichloromethane (0.1 mol/L) following the same protocol as that described in section 1.6 hereinabove for the synthesis of the carbamide TrEHU. This gives 1.84 g of the carbamide DEHOU in the form of a colourless oil (Yield: 94%). The characterisations of this carbamide are given hereinafter $^1$H NMR (CDCl$_3$, 400 MHz) δ (ppm): 4.25 (t, J=4.9 Hz, 1H); 3.20 (q, J=6.1 Hz, 2H); 3.07 (m, 4H); 1.61 (hept, J=5.6 Hz, 2H); 1.46 (quint, J=6.4 Hz, 2H); 1.25 (m, 26H); 0.86 (m, 15H)

$^{13}$C NMR (CDCl$_3$, 101 MHz) δ (ppm): 158.3; 51.5; 41.0; 38.5; 31.9; 30.8; 30.5; 29.5; 29.4; 29.0; 27.2; 24.1; 23.2; 22.8; 14.2; 10.9

IR (KBr, v$_{max}$/cm$^{-1}$): 3344; 2957; 2924; 2857; 1618; 1533; 1459; 1408; 1378; 1241; 765; 725

MS (positive mode ESI): 397 (MH$^+$); 816 (2MNa$^+$)

HRMS (positive mode ESI): calculated for C$_{25}$H$_{53}$N$_2$O: 397.4158; obtained: 397.4154

Elemental analysis (%) (C$_{25}$H$_{52}$N$_2$O): calculated: C, 75.69; H, 13.21; N, 7.06; obtained: C, 75.87; H, 13.49; N, 6.89

I.8—N-cyclohexyl-N',N'-di-n-octylurea or CyDOU:

The carbamide CyDOU, which complies with the formula (I) hereinabove wherein R$^1$=R$^2$=n-octyl, R$^3$=cyclohexyl and R$^4$=H, is synthesised from di-n-octylamine (1.50 mL, 4.87 mmol, 1 eq.) and cyclohexylisocyanate (1.27 mL, 9.74 mmol, 2 eq.) in anhydrous dichloromethane (0.1 mol/L) following the same protocol as that described in section 1.6 hereinabove for the synthesis of the carbamide TrEHU with the exception that the dichloromethane/ethyl acetate used for the flash chromatography on silica gel with a gradient is from 96/4 to 90/10, v:v. This gives 1.48 g of the carbamide CyDOU in the form of a colourless oil (Yield: 83%). The characterisations of this compound are given hereinafter.

$^1$H NMR (CDCl$_3$, 400 MHz) δ (ppm): 4.11 (s, 1H); 3.64 (m, 1H); 3.13 (t, J=7.6 Hz, 4H); 1.94 (m, 2H); 1.59 (m, 8H); 1.28 (m, 24H); 0.87 (t, 6H)

$^{13}$C NMR (CDCl$_3$, 101 MHz) δ (ppm): 157.1; 49.3; 47.5; 34.3; 32.0; 29.6; 29.4; 28.8; 27.2; 25.9; 25.2; 22.8; 14.2

IR (KBr, $v_{max}$/cm$^{-1}$): 3330; 2922; 2853; 1617; 1528; 1451; 1407; 1314; 1251; 1214; 890; 767; 722

MS (positive mode ESI): 367 (MH$^+$); 756 (2MNa$^+$)

HRMS (positive mode ESI): calculated for $C_{23}H_{47}N_2O$: 367.3688; obtained: 367.3686

Elemental analysis (%) ($C_{23}H_{46}N_2O$): calculated: C, 75.35; H, 12.65; N, 7.64; obtained: C, 75.33; H, 12.80; N, 7.47

II—Extractant Properties of the Carbamides

II.1—Tetraalkylated Carbamides:
Uranium(VI) and Plutonium(IV) Extraction Tests:
Extraction tests are carried out using:
as organic phases: solutions comprising either ≈0.5 mol/L or ≈1.2 mol/L of one of the carbamides TBU, THU, TOU, TPU, DBDHU, DHDPU, sym-DEDOU and DMDNU in TPH; and
as aqueous phases: aqueous solutions comprising 10 g/L of uranium(VI), ≈200 kBq/mL of plutonium(IV) and nitric acid at a concentration either of 4 mol/L (to simulate the acidity liable to be exhibited by an aqueous solution issued from the dissolution of a spent nuclear fuel in nitric acid) or of 0.5 mol/L (to simulate the acidity that would be exhibited by the aqueous solution liable to be used to strip the plutonium according to the invention).

Each of these tests is carried out by contacting, in a tube and with stirring, an organic phase with an aqueous phase for 30 minutes at 25° C. The volume ratio O/A is 1.

After centrifugation and separation of the phases, the uranium concentrations are measured in the aqueous phases by inductively coupled plasma atomic emission spectrometry (or ICP-AES) whereas the uranium concentrations in the organic phases are determined by stripping this element in a nitric acid solution at a concentration of 0.01 mol/L and by measuring by ICP-AES the concentration thereof in the aqueous phase resulting from this stripping. The plutonium concentrations are measured in the aqueous and organic phases by α spectrometry.

Table I hereinafter shows, for each carbamide tested and for each concentration at which this carbamide was tested, the distribution coefficients of uranium, annotated $D_U$, and of plutonium, annotated $D_{Pu}$, as obtained for the aqueous phases at 4 mol/L HNO$_3$ and at 0.5 mol/L HNO$_3$ as well as the separation factors U/Pu, annotated $FS_{U/Pu}$, as obtained for the aqueous phases at 0.5 mol/L HNO$_3$.

By way of comparison, are also reported in this table the results of extraction tests carried out under the same operating conditions but using as organic phases, solutions comprising N,N-dialkylamides according to the prior art, namely:
a solution comprising 0.5 mol/L of DEHDMBA (N,N-di(2-ethyhexyl)-3,3-dimethybutyramide) proposed in reference [1], in TPH; and
a solution comprising either 0.5 mol/L or 1.2 mol/L of MOEHA (N-methyl-N-octyl-2-ethylhexanamide) proposed in reference [2], in TPH.

TABLE I

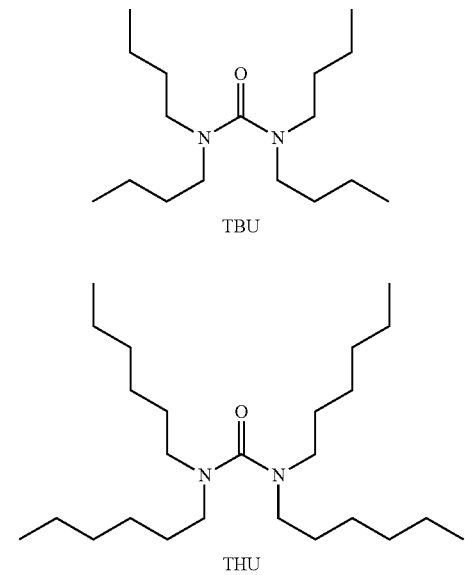

| Compounds under test | [C] (mol/L) | [HNO$_3$] (mol/L) | $D_U$ | $D_{Pu}$ | $FS_{U/Pu}$ |
|---|---|---|---|---|---|
| TBU | 0.48 | 4 | 2.8 | 0.15 | |
| | | 0.5 | 0.11 | 0.004 | 26 |
| | 1.2 | 4 | 15.9 | 3.8 | |
| | | 0.5 | 0.96 | 0.027 | 36 |
| THU | 0.51 | 4 | 4.0 | 0.33 | |
| | | 0.5 | 0.15 | 0.009 | 16 |
| | 1.3 | 4 | 17.5 | 2.6 | |
| | | 0.5 | 1.0 | 0.045 | 23 |

TABLE I-continued
| Compounds under test | [C] (mol/L) | [HNO₃] (mol/L) | $D_U$ | $D_{Pu}$ | $FS_{U/Pu}$ |
|---|---|---|---|---|---|
| 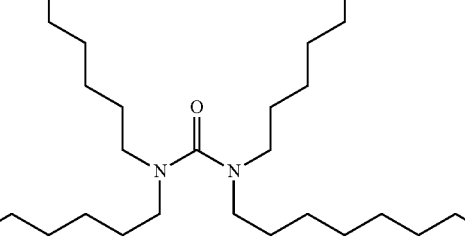 TOU | 0.52<br>1.2 | 4<br>0.5<br>4<br>0.5 | 5.1<br>0.26<br>16.5<br>1.1 | 1.3<br>0.048<br>1.9<br>0.33 | 5.4<br>3.4 |
| 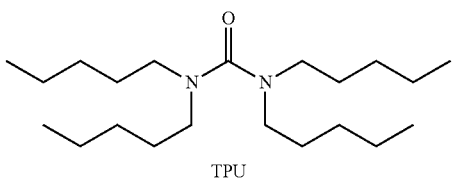 TPU | 1.2 | 4<br>0.5 | 18.4<br>0.80 | 2.15<br>0.011 | 73 |
| 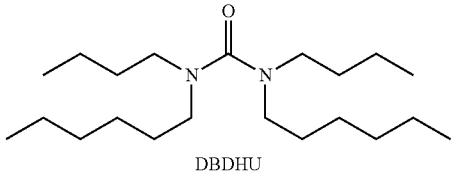 DBDHU | 1.2 | 4<br>0.5 | 18.7<br>0.77 | 2.22<br>0.010 | 74 |
| 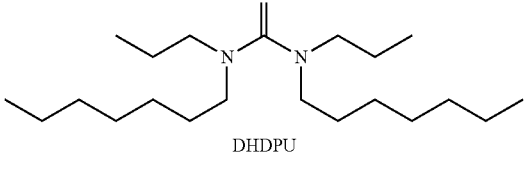 DHDPU | 1.2 | 4<br>0.5 | 18.8<br>0.74 | 2.37<br>0.008 | 94 |
| 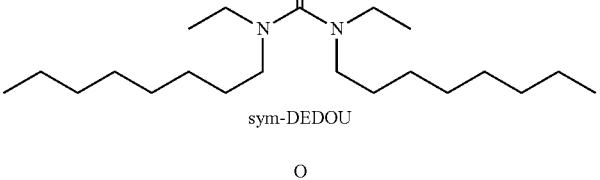 sym-DEDOU | 1.2 | 4<br>0.5 | 18.5<br>0.68 | 1.32<br>0.004 | 170 |
| 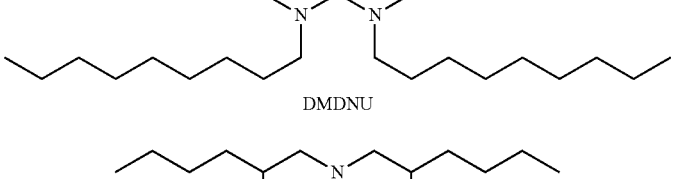 DMDNU | 1.3 | 4<br>0.5 | 39.1<br>2.74 | 33.5<br>0.092 | 30 |
| 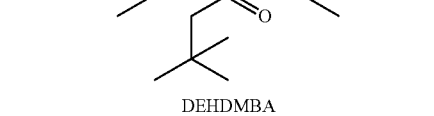 DEHDMBA | 0.50 | 4<br>0.5 | 2.5<br>0.036 | 0.31<br>0.003 | 13 |

TABLE I-continued

| Compounds under test | [C] (mol/L) | [HNO$_3$] (mol/L) | D$_U$ | D$_{Pu}$ | FS$_{U/Pu}$ |
|---|---|---|---|---|---|
| MOEHA (structure shown) | 0.50 | 4 | 1.9 | 0.22 | |
| | | 0.5 | 0.050 | 0.004 | 13 |
| | 1.2 | 4 | 7.5 | 4.3 | |
| | | 0.5 | 0.31 | 0.016 | 20 |

[C] = concentration of the compound under test in the organic phase
[HNO$_3$] = concentration of nitric acid in the aqueous phase This table shows that, whether at strong acidity ([HNO$_3$]=4 mol/L) or at moderate acidity ([HNO$_3$]=0.5 mol/L), the distribution coefficients of uranium(VI) obtained for the eight tetraalkylated carbamides tested are all greater than those obtained for the N,N-dialkylamides DEHDMBA and MOEHA, at a similar concentration in organic phase, which confirms the strong ability of tetraalkylated carbamides to extract uranium(VI) from a strongly acidic aqueous phase.

In particular, whether at strong acidity ([HNO$_3$]=4 mol/L) or at moderate acidity ([HNO$_3$]=0.5 mol/L), the distribution coefficients of uranium(VI) obtained for the carbamides TPU, DBDHU, DHDPU, sym-DEDOU and DMDNU at a concentration of the order of 1.2 mol/L in organic phase are more than two times greater than those obtained for a similar concentration of MOEHA in organic phase.

This table also shows that at strong acidity ([HNO$_3$]=4 mol/L) and for a concentration of 0.5 mol/L in organic phase, the carbamides TBU and TOU also result in distribution coefficients of plutonium(IV) which are greater than those obtained for a similar concentration of DEHDMBA and MOEHA in organic phase.

On the other hand, for a concentration of 1.2 mol/L in organic phase, the carbamides TBU, THU, TOU, TPU, DBDHU, DHDPU and sym-DEDOU result in distribution coefficients of plutonium(IV) which are less than that obtained for a similar concentration of MOEHA in organic phase but these distribution coefficients remain nonetheless very satisfactory since those of the carbamides TBU, THU, TPU, DBDHU and DHDPU are greater than 2, that of the carbamide TOU is close to 2 (D$_{Pu}$=1.9) and that of sym-DEDOU is greater than 1.3.

This table further shows that at moderate acidity ([HNO$_3$]=0.5 mol/L), the U(VI)/Pu(IV) separation factors obtained for the carbamides TBU, THU, TPU, DBDHU, DHDPU, sym-DEDOU and DMDNU are greater than those obtained for the N,N-dialkylamides DEHDMBA and MOEHA, at similar concentration in organic phase.

In particular, when they are used at a rate of 1.2 mol/L in organic phase, TBU makes it possible to attain a U(VI)/Pu(IV) separation factor of 36, i.e. almost 2 times higher than that obtained for MOEHA at a similar concentration in organic phase; the carbamides TPU and DBDHU make it possible to attain U(VI)/Pu(IV) separation factors respectively of 73 and 74, i.e. almost 4 times higher than that obtained for MOEHA; the carbamide DHDPU makes it possible to attain a U(VI)/Pu(IV) separation factor of 94, i.e. almost 5 times higher than that obtained for MOEHA; as regards the U(VI)/Pu(IV) separation factor obtained for sym-DEDOU, it is 8.5 times higher than that obtained for MOEHA (170 versus 20).

This table confirms therefore that the tetraalkylated carbamides can advantageously be used as extractants in a method for treating an aqueous solution issued from the dissolution of a spent nuclear fuel in nitric acid, comprising a co-extraction of uranium(VI) and plutonium(IV) from this aqueous solution, which is strongly acidic, followed by partial or total separation of the plutonium(IV) from the uranium(VI) present in the organic phase issued from this co-extraction by stripping plutonium(IV) from this organic phase by means of an aqueous solution of moderate acidity.

Of these tetraalkylated carbamides, the carbamide DMDNU appears to be of particular interest for the development of such a method since, on one hand, it exhibits, at strong acidity, a significantly higher ability to extract uranium (D$_U$ and D$_{Pu}$>30) than that of MOEHA (D$_U$=7.5 and D$_{Pu}$=4.3) and, on the other, it results, at moderate acidity, in a uranium(VI)/plutonium(IV) separation factor (FS$_{U/Pu}$=30) which is also significantly higher than that obtained with MOEHA.

Although it exhibits, at strong acidity, a lower ability to extract plutonium than that of MOEHA, the carbamide sym-DEDOU also appears to be a good candidate since it makes it possible to attain, at moderate acidity, a particularly high uranium(VI)/plutonium(IV) separation factor (F$_{SU/Pu}$=170).

Uranium(VI) Charge Capacity Tests:

Uranium(VI) charge capacity tests are carried out by contacting 4 times, in tubes and with stirring, organic phases comprising 1.2 mol/L of one of the carbamides TPU, DBDHU, DHDPU, sym-DEDOU and DMDNU in TPH with aliquots of an aqueous phase comprising 200 g/L uranium(VI) and 3.4 mol/L nitric acid.

Each contact is carried out at 25° C., for 30 minutes and with an O/A ratio of 2.

After centrifugation and separation of the phases, the uranium concentrations are measured in the organic phases after stripping this element in a nitric acid solution at a concentration of 0.01 mol/L and by measuring by ICP-AES the concentration thereof in the aqueous phase resulting from this stripping.

Table II hereinafter shows, for each carbamide tested, the concentrations of uranium(VI), expressed in g/L, as obtained in the organic phases after each of the 4 contacts.

By way of comparison, are also reported in this table the results of charge capacity tests carried out under the same operating conditions but using as organic phases, solutions comprising 1.2 mol/L of MOEHA in TPH.

TABLE II

| Compounds under test | Uranium(VI) concentration in organic phases (g/L) | | | |
|---|---|---|---|---|
| | Contact 1 | Contact 2 | Contact 3 | Contact 4 |
| TPU | 88 | 124 | 134 | 143 |
| DBDHU | 91 | 127 | 131 | 131 |
| DHDPU | 91 | 129 | 136 | 136 |
| sym-DEDOU | 91 | 125 | 138 | 130 |
| DMDNU | 95 | 133 | 138 | 137 |
| MOEHA | 87 | 124* | — | — |

*After dilution of the 3$^{rd}$ phase

After a second contacting, the organic phase containing MOEHA forms a 3$^{rd}$ phase. Adding 300 μL of organic phase (pre-equilibrated by contacting with nitric acid) makes it possible to remove this 3$^{rd}$ phase: saturation of the organic phase with uranium(VI) is therefore attained for 124 g/L, i.e. about 87% of the theoretical charge capacity of the organic phase (taking into consideration a uranium/extractant stoichiometry of 1/2).

On the other hand, under the same conditions, the carbamides do not demix and it is possible to charge an organic phase comprising a carbamide with 130 g/L to 143 g/L of uranium(VI), which represents more than 88% of the theoretical charge capacity of the organic phase (taking into consideration a uranium/extractant stoichiometry of 1/2).

These results show that the carbamides have a high uranium(VI) charge capacity, compatible with the development of a method for treating nuclear fuels, and that they even make it possible to prevent organic phase demixing problems liable to be observed with MOEHA.

II.2—Trialkylated Carbamides:

Extraction tests identical to those described in section II.1 hereinabove are carried out but using as organic phases, solutions comprising from 0.4 mol/L to 0.5 mol/L of one of the carbamides TrOU, TrEHU and DEHOU in TPH.

The results of these tests are shown in table III hereinafter.

By way of comparison, are also reported in this table the results previously reported in table 1 hereinabove for MOEHA at 0.5 mol/L in TPH.

TABLE III

| Compounds under test | [C] (mol/L) | [HNO$_3$] (mol/L) | D$_U$ | D$_{Pu}$ | FS$_{U/Pu}$ |
|---|---|---|---|---|---|
| 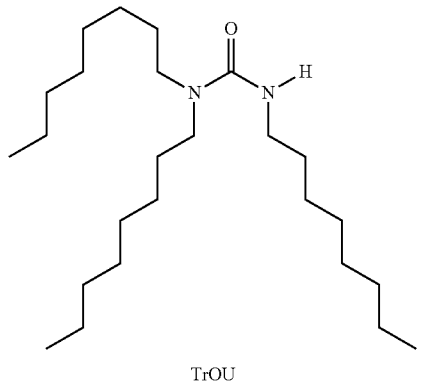 [SMILES: CCCCCCCCNC(=O)N(CCCCCCCC)CCCCCCCC ; "TrOU"] TrOU | 0.52 | 4 | 22 | 6.0 | |
| | | 0.5 | 2.7 | 0.037 | 72 |
| 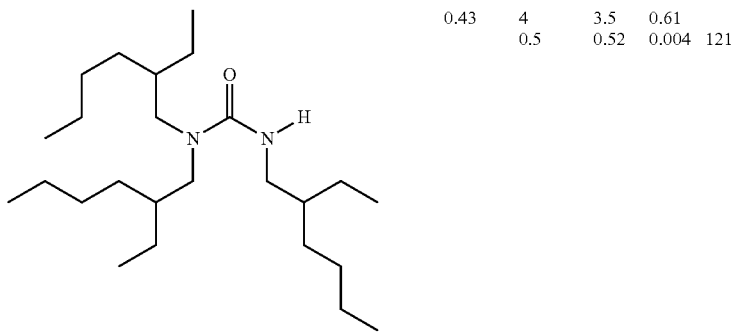 TrEHU | 0.43 | 4 | 3.5 | 0.61 | |
| | | 0.5 | 0.52 | 0.004 | 121 |

TABLE III-continued

| Compounds under test | [C] (mol/L) | [HNO$_3$] (mol/L) | D$_U$ | D$_{Pu}$ | FS$_{U/Pu}$ |
|---|---|---|---|---|---|
| DEHOU | 0.44 | 4 | 5.4 | 1.7 | |
|  |  | 0.5 | 0.63 | 0.026 | 24 |
| MOEHA | 0.5 | 4 | 1.9 | 0.22 | |
|  |  | 0.5 | 0.050 | 0.004 | 13 |

[C] = concentration of the compound under test in the organic phase
[HNO$_3$] = concentration of nitric acid in the aqueous phase This table shows that at strong acidity ([HNO$_3$]=4 mol/L), the three trialkylated carbamides tested extract uranium(VI) and plutonium(IV) more substantially than N,N-dialkylamide MOEHA since they result in distribution coefficients of uranium(VI) and plutonium(IV) which are all greater than those obtained for this N,N-dialkylamide.

It also shows that at moderate acidity ([HNO$_3$]=0.5 mol/L), the three trialkylated carbamides tested make it possible to retain uranium(VI) in organic phase, both very effectively (D$_U$>0.5) and selectively relative to plutonium(IV) since the distribution coefficient of plutonium(IV) obtained for these carbamides is less than 0.04.

The carbamide TrEHU is particularly selective since this carbamide makes it possible to attain a U(VI)/Pu(IV) separation factor of 121, i.e. almost 10 times higher than that attained for N,N-dialkylamide MOEHA at a comparable concentration.

Here again, this table confirms that the trialkylated carbamides can advantageously be used as extractants in a method for treating an aqueous solution issued from the dissolution of a spent nuclear fuel in nitric acid, comprising a co-extraction of uranium(VI) and plutonium(IV) from this aqueous solution, which is strongly acidic, followed by partial or total separation of the plutonium(IV) from the uranium(VI) present in the organic phase issued from this co-extraction by stripping plutonium(IV) from this organic phase by means of an aqueous solution of moderate acidity.

III—Principle Diagram of a Preferred Embodiment of the Use of the Invention

Reference is made to the drawing FIGURE which represents a principle diagram of a preferred embodiment of the use of the invention.

As this FIGURE shows, this use comprises 4 steps.

The first of these steps, annotated "U+Pu co-extraction" in the drawing FIGURE, is intended to extract jointly uranium (VI) and plutonium(IV) from an aqueous nitric spent nuclear fuel dissolution solution, annotated "A1" in the drawing FIGURE.

Such a solution typically comprises from 3 mol/L to 6 mol/L of HNO$_3$, uranium, plutonium, minor actinides (particularly americium and curium), fission products (La, Ce, Pr, Nd, Sm, Eu, Gd, Mo, Zr, Ru, Tc, Rh, Pd, Y, Cs, Ba, etc.) as well as some corrosion products such as iron.

The "U+Pu co-extraction" step is carried out by circulating, in the extractor 1, the aqueous solution A1 in counterflow to an organic phase, annotated "S1" in the drawing FIGURE, which comprises from 0.5 mol/L to 2 mol/L and, more preferably, from 1.0 mol/L to 1.4 mol/L, of a carbamide of general formula (I), in solution in an organic diluent.

This organic diluent is advantageously an acyclic hydrocarbon or a mixture of acyclic hydrocarbons, for example n-dodecane, hydrogenated tetrapropylene (TPH), kerosene, Isane™ IP-185T or Isane™ IP-175T, preference being given to TPH.

The second step, annotated "PF washing" in the drawing FIGURE, is intended to strip from the organic phase issued from the "U+Pu co-extraction" the fraction of fission products extracted from the aqueous solution A1 jointly with uranium(VI) and plutonium(IV).

To do this, the "PF washing" step comprises one or a plurality of washing operations of the organic phase issued from the "U+Pu co-extraction", each washing operation being carried out, in the extractor 2, in counterflow to an aqueous solution, annotated "A3" in the drawing FIGURE, comprising nitric acid and wherein the HNO$_3$ concentration can range from 1 mol/L to 6 mol/L but is, preferably, from 4 mol/L to 6 mol/L.

If the "PF washing" step is carried out with a strongly acidic aqueous solution, i.e. typically equal to or greater than 3 mol/L of $HNO_3$, then this step further comprises a deacidification of the organic phase, carried out by circulating this organic phase in counterflow to a weakly acidic aqueous solution, annotated "A4" in the drawing FIGURE, i.e. comprising from 0.1 mol/L to 1 mol/L of $HNO_3$ such as an aqueous solution comprising 0.5 mol/L of $HNO_3$, so as to prevent an excessive quantity of acid being carried to the extractor intended for the third step, annotated "Pu stripping" in the drawing FIGURE, and does not disturb the performances of this third step.

The "Pu stripping" step is intended to strip plutonium with a degree of +IV oxidation from the organic phase issued from the "PF washing".

It is carried out by circulating, in the extractor 3, this organic phase in counterflow to an aqueous solution, annotated "A2" in the drawing FIGURE, comprising from 0.1 mol/L to 0.5 mol/L of $HNO_3$ and using, preferably, a flow rate ratio O/A greater than 1, preferably equal to or greater than 3 and, more preferably, equal to or greater than 5 so that plutonium(IV) is stripped in a concentrating manner.

The stripping of plutonium(IV), which is carried out in the "Pu stripping" step, is accompanied by a stripping of a fraction of uranium(VI) which is also present in the organic phase issued from the "PF washing".

Therefore, the fourth step, annotated "U washing" in the drawing FIGURE is intended to extract from the aqueous phase issued from the "Pu stripping":

either all of the uranium(VI) present in this aqueous phase if it is sought to obtain, following this step, an aqueous solution comprising plutonium(IV) without uranium (VI);

or the quantity of uranium(VI) suitable for obtaining, following this step, an aqueous solution comprising uranium(VI) and plutonium(IV) in a pre-selected ratio.

In both cases, the "U washing" is carried out by circulating, in the extractor 4, the aqueous phase issued from the "Pu stripping" in counterflow to an organic phase, annotated "S2" in the drawing FIGURE, the qualitative and quantitative composition whereof is, preferably, identical to that of the organic phase S1. The quantity of uranium(VI) extracted is set by adjusting, on one hand, the flow rate ratio O/A, and, on the other hand, the acidity of the aqueous phase, uranium (VI) being, indeed, extracted all the better if the ratio of the organic phase/aqueous phase flow rates and the acidity of the aqueous phase are high. Adding more or less concentrated $HNO_3$ to the aqueous phase circulating in the extractor 4 can therefore be envisaged according to the acidity that it is sought to give this aqueous phase.

Following these 4 steps, are obtained:

a raffinate, which corresponds to the aqueous phase from the extractor 1 and which comprises fission products as well as americium and curium;

the aqueous phase issued from the extractor 4, which comprises either decontaminated plutonium(IV) or a mixture of decontaminated plutonium(IV) and uranium (VI); and the organic phase issued from the extractor 3, which comprises uranium(VI) without plutonium(IV).

This organic phase may be routed, directly or after further treatments, to an extractor, not shown in the drawing FIGURE, wherein uranium(VI) will be stripped from this organic phase, for example by means of an aqueous solution comprising at most 0.05 mol/L of $HNO_3$ such as an aqueous solution comprising 0.01 mol/L of $HNO_3$, at ambient temperature (i.e. at 20-25° C.) or hot (i.e. typically at a temperature of 40-50° C.) and using, preferably, a flow rate ratio O/A greater than 1 so that uranium(VI) is stripped in a concentrating manner.

REFERENCES CITED

[1] International PCT application WO 2017/017207
[2] International PCT application WO 2017/017193
[3] E. K. Dukes and T. H. Sidall, *Journal of Inorganic and Nuclear Chemistry* 1966, 28(10), 2307-2312
[4] G. M. Chumakova et al., *Radiokhimiya* 1980, 22(2), 213-217
[5] B. G. Vats et al., *Dalton Transactions* 2016, 45(25), 10319-10325

What is claimed is:

1. A method for totally or partially separating uranium (VI) from plutonium(IV), without reducing plutonium(IV) to plutonium(III), from an aqueous solution A1 issued from the dissolution of a spent nuclear fuel in nitric acid, comprising:

a) a co-extraction of uranium(VI) and plutonium(IV) from the aqueous solution A1, the co-extraction comprising at least one contacting, in an extractor, of the aqueous solution with an organic solution S1 comprising a carbamide as an extractant in an organic diluent, followed by separating the aqueous solution from the organic solution, the carbamide being of formula(I):

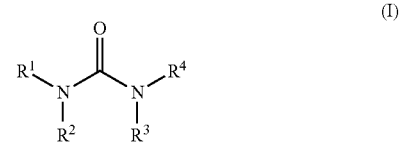

wherein:

$R^1$, $R^2$ and $R^3$, identical or different, represent a linear or branched alkyl group, comprising from 1 to 12 carbon atoms, a cycloalkyl group comprising from 3 to 12 carbon atoms or a cycloalkylalkyl group comprising from 4 to 13 carbon atoms;

$R^4$ represents a hydrogen atom, a linear or branched alkyl group, comprising from 1 to 12 carbon atoms, a cycloalkyl group comprising from 3 to 12 carbon atoms or a cycloalkylalkyl group comprising from 4 to 13 carbon atoms;

b) a stripping of plutonium(IV) and a fraction of uranium (VI) from the organic solution issued from a), the stripping comprising at least one contacting, in an extractor, of the organic solution with an aqueous solution A2 comprising from 0.1 mol/L to 0.5 mol/L of nitric acid, followed by separating the organic solution from the aqueous solution; and c) an extraction of all or part of the uranium(VI) fraction present in the aqueous solution issued from b), the extraction comprising at least one contacting, in an extractor, of the aqueous solution with an organic solution S2 comprising the carbamide in an organic diluent, followed by separating the aqueous solution from the organic solution;

whereby an aqueous solution comprising plutonium(IV) without uranium(VI) or a mixture of plutonium(IV) and uranium(VI), and an organic solution comprising uranium (VI) without plutonium(IV) are obtained.

2. The method of claim 1, in which the carbamide comprises a total number of carbon atoms between 17 and 25.

3. The method of claim 1, in which $R^1$, $R^2$, $R^3$ and $R^4$ represent a linear or branched alkyl group, comprising from 1 to 12 carbon atoms.

4. The method of claim 1, in which $R^1$ and $R^2$ are identical and represent a linear or branched alkyl group, comprising from 1 to 5 carbon atoms, $R^3$ and $R^4$ are identical and represent a linear or branched alkyl group, comprising from 6 to 10 carbon atoms, and the carbamide comprises a total number of carbon atoms equal to 19, 21 or 23.

5. The method of claim 1, in which $R^1$ and $R^4$ are identical and represent a linear or branched alkyl group, comprising from 1 to 5 carbon atoms, $R^2$ and $R^3$ are identical et represent a linear or branched alkyl group, comprising from 6 to 10 carbon atoms, and the carbamide comprises a total number of carbon atoms equal to 19, 21 or 23.

6. The method of claim 1, in which $R^1$, $R^2$, $R^3$ and $R^4$ are identical and represent a linear or branched alkyl group comprising from 4 to 8 carbon atoms.

7. The method of claim 1, in which $R^1$, $R^2$ and $R^3$ represent a linear or branched alkyl group, comprising from 1 to 12 carbon atoms and $R^4$ represents a hydrogen atom.

8. The method of claim 1, in which $R^1$, $R^2$ and $R^3$ are identical and represent a linear or branched alkyl group, comprising from 6 to 8 carbon atoms.

9. The method of claim 1, in which the carbamide is N,N,N'-tri-n-octylurea, N,N,N'-tri(2-ethylhexyl)urea, N,N-di(2-ethylhexyl)-N'-n-octylurea, N,N,N',N'-tetra-n-butylurea, N,N,N',N'-tetra-n-pentylurea, N,N,N',N'-tetra-n-hexylurea, N,N,N',N'-tetra-n-octylurea, N,N'-di-n-butyl-N,N'-di-n-hexylurea, N,N'-di-n-heptyl-N,N'-di-n-propylurea, N,N'-diethyl-N,N'-di-n-octylurea or N,N'-dimethyl-N,N'-di-n-nonylurea.

10. The method of claim 1, in which the organic solutions S1 and S2 comprise from 0.5 mol/L to 2 mol/L of the carbamide.

11. The method of claim 1, in which a) further comprises a decontamination of the organic solution issued from the co-extraction of uranium(VI) and plutonium(IV) with respect of americium, curium and fission products, the decontamination comprising at least one contacting, in an extractor, of the organic solution with an aqueous solution A3 comprising from 1 mol/L to 6 mol/L of nitric acid, followed by separating the organic solution from the aqueous solution.

12. The method of claim 1, in which the contacting, in the extractor of b), of the organic solution issued from a) with the aqueous solution A2 comprises a counterflow circulation of the organic solution and the aqueous solution A2 with a flow rate ratio O/A which is greater than 1.

13. The method of claim 1, which further comprises a stripping of uranium(VI) from the organic solution issued from c), the stripping comprising at least one contacting of the organic solution with an aqueous solution A5 comprising at most 0.05 mol/L of nitric acid, followed by separating the organic solution from the aqueous solution.

\* \* \* \* \*